United States Patent
Ellis et al.

(10) Patent No.: US 11,032,887 B2
(45) Date of Patent: Jun. 8, 2021

(54) SYSTEMS AND METHODS FOR APPLYING ULTRAVIOLET LIGHT

(71) Applicant: RGF ENVIRONMENTAL GROUP, INC., Riviera Beach, FL (US)

(72) Inventors: Walter B. Ellis, Jupiter, FL (US); Sergei Chtchavelev, Greenacres, FL (US)

(73) Assignee: RGF ENVIRONMENTAL GROUP, INC., Riviera Beach, FL (US)

( * ) Notice: Subject to any disclaimer, the term of this patent is extended or adjusted under 35 U.S.C. 154(b) by 55 days.

(21) Appl. No.: 16/704,174

(22) Filed: Dec. 5, 2019

(65) Prior Publication Data

US 2020/0188544 A1   Jun. 18, 2020

Related U.S. Application Data

(60) Provisional application No. 62/781,220, filed on Dec. 18, 2018.

(51) Int. Cl.
*H05B 45/335* (2020.01)
*H05B 45/33* (2020.01)
(Continued)

(52) U.S. Cl.
CPC .............. *H05B 45/335* (2020.01); *A61L 2/10* (2013.01); *B01D 53/007* (2013.01); *C02F 1/325* (2013.01);
(Continued)

(58) Field of Classification Search
CPC ...... H05B 45/335; H05B 45/10; H05B 45/33; B01D 53/007; B01D 2259/804;
(Continued)

(56) References Cited

U.S. PATENT DOCUMENTS 10,598,332 B1 * 3/2020 Elwell ................. B60Q 1/0041
2002/0113246 A1   8/2002 Nagai et al.
(Continued)

FOREIGN PATENT DOCUMENTS

WO   2013160834 A2   10/2013

OTHER PUBLICATIONS

International Search Report and the Written Opinion of the International Searching Authority, issued in corresponding International Application No. PCT/US2019/065094, dated Jun. 9, 2020, 19 pages.
(Continued)

*Primary Examiner* — Brooke Purinton
(74) *Attorney, Agent, or Firm* — Rothwell, Figg, Ernst & Manbeck, P.C.

(57) ABSTRACT

Systems and methods for applying light to an environment are provided. A system may include an elongate first body having a first side wall, a second side wall opposite the first side wall, and a bottom wall. The first body may define a lengthwise channel between the first side wall and the second side wall. The first body may have a first groove disposed along an inner surface of the first side wall, a second groove disposed along an inner surface of the second side wall, and a cover which may be coupled to the first body via the first groove and the second groove. The first body and the cover may collectively enclose at least a portion of the channel. The system may include an LED disposed within the channel.

20 Claims, 8 Drawing Sheets

(51) Int. Cl.
*A61L 2/10* (2006.01)
*F21S 4/28* (2016.01)
*F21V 29/83* (2015.01)
*F21V 29/503* (2015.01)
*B01D 53/00* (2006.01)
*C02F 1/32* (2006.01)

(52) U.S. Cl.
CPC .............. *F21S 4/28* (2016.01); *F21V 29/503* (2015.01); *F21V 29/83* (2015.01); *H05B 45/33* (2020.01); *A61L 2202/11* (2013.01); *B01D 2259/804* (2013.01); *C02F 2201/3222* (2013.01); *C02F 2201/3225* (2013.01); *C02F 2201/3227* (2013.01)

(58) Field of Classification Search
CPC ...... C02F 2201/3222; C02F 2201/3225; C02F 2201/3227; C02F 2201/326; C02F 1/325; F24F 8/22; A61L 2202/14; A61L 2/24; A61L 2209/11; A61L 2209/16; A61L 9/20; A61L 2/10; A61L 2202/11; H01L 25/0753; F21Y 2115/10; F21S 2/00; F21S 4/28; F21V 21/00; F21V 29/83; F21V 29/503
See application file for complete search history.

(56) References Cited

U.S. PATENT DOCUMENTS

| | | |
|---|---|---|
| 2005/0186124 A1 | 8/2005 | Fink et al. |
| 2009/0152569 A1 | 6/2009 | Cheng et al. |
| 2010/0103672 A1 | 4/2010 | Thomas et al. |
| 2013/0094200 A1* | 4/2013 | Dellian .................. F21V 29/70 362/218 |
| 2016/0309552 A1 | 10/2016 | Kuerschner et al. |
| 2017/0280521 A1 | 9/2017 | Shan |
| 2017/0352605 A1* | 12/2017 | Bilan .................. H01L 23/3672 |
| 2019/0142987 A1* | 5/2019 | Zhang ...................... C02F 1/32 250/435 |
| 2019/0234564 A1* | 8/2019 | Han ........................ F21K 9/272 |
| 2020/0088396 A1* | 3/2020 | Duan ...................... F21K 9/232 |
| 2020/0208829 A1* | 7/2020 | Lee .......................... F21V 15/01 |
| 2021/0033273 A1* | 2/2021 | Hendricks ................. F21S 4/28 |

OTHER PUBLICATIONS

Invitation to Pay Additional Fees, Partial International Serch of the International Searching Authority, issued in corresponding International Application No. PCT/US2019/065094, dated Mar. 18, 2020, 10 pages.

Office Action issued for US. Appl. No. 16/704,179 dated Apr. 17, 2020, 14 pages.

* cited by examiner

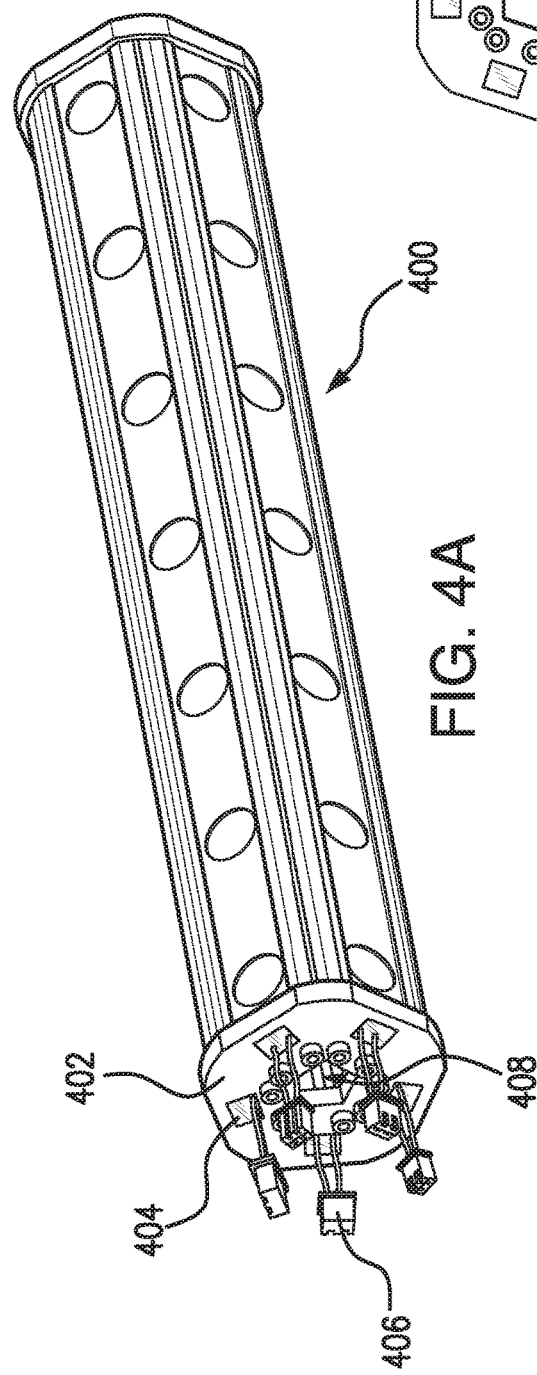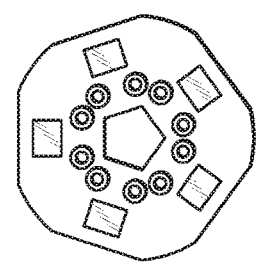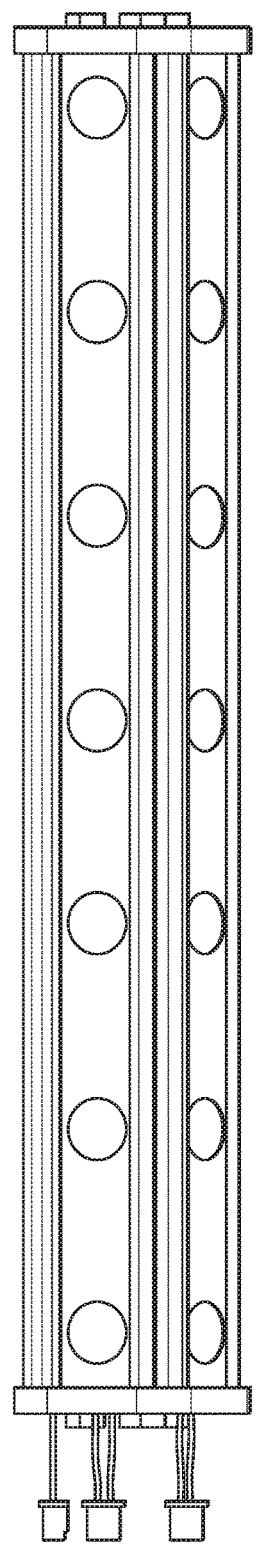
FIG. 4A
FIG. 4C
FIG. 4B

SYSTEMS AND METHODS FOR APPLYING ULTRAVIOLET LIGHT

PRIORITY CLAIM AND CROSS-REFERENCE TO RELATED APPLICATIONS

The present application claims priority to U.S. Provisional Patent Application Ser. No. 62/781,220, filed Dec. 18, 2018, which is hereby incorporated by reference in its entirety. This application is related to U.S. patent application Ser. No. 16/704,179 titled "SYSTEMS AND METHODS FOR APPLYING ULTRAVIOLET LIGHT," being filed concurrently herewith and incorporated herein by reference.

FIELD OF THE DISCLOSURE

This disclosure relates to systems and methods for applying ultraviolet (UV) light to an environment.

BACKGROUND

There are many cases in which UV light may be applied to an environment. For example, U.S. Pat. Nos. 7,988,923 and 9,884,312, both incorporated herein by reference in their entireties, describe applying UV light to effect an oxidation reaction and/or deactivate microorganisms such as germs, viruses, and bacteria. Such UV light may be applied, for example, in a heating, ventilation, or air conditioning (HVAC) system (e.g., in an AC duct system) to clean or purify air in an environment. In other cases, UV light may be applied within a liquid (e.g., water) to clear or purify that liquid.

Light emitting diodes (LEDs) are efficient devices for applying UV light, including the wavelengths of UV light that may be used to purify an environment. UV LEDs can, however, discharge significant heat which, if not dissipated, can interfere with the operation of the UV LED. Moreover, the significant heat generated by the LEDs and the cycling of such LEDs on and off may result in significant expansion and contraction of the structure configured to house the LEDs. Moreover, LEDs have relatively low tolerance for humidity and may fail if exposed to a humid environment for an extended period of time.

Therefore, a need exists to provide cost-effective systems and methods for housing LED lights that are capable of dissipating the heat generated by the LEDs and have sufficient mechanical and chemical durability to withstand the constant temperature fluctuations, while simultaneously protecting the LEDs and allowing the LED lights to be used to purify air or liquid in a wide range of environments.

Moreover, a need exists to provide systems and methods for controlling LEDs capable of minimizing heat generation and power consumption while simultaneously prolonging LED life and maximizing the effectiveness of the UV light generated by LEDs to clean and purify air and liquid.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

In some embodiments, a system for applying light to an environment may be provided. The system may include an elongate first body having a first side wall, a second side wall opposite the first side wall, and a bottom wall. The first body may define a lengthwise channel between the first side wall and the second side wall. The first body may have a first groove disposed along an inner surface of the first side wall, a second groove disposed along an inner surface of the second side wall, and a cover which may be coupled to the first body via the first groove and the second groove. The first body and the cover may collectively enclose at least a portion of the channel. The system may include an LED disposed within the channel. A window may be disposed in the cover adjacent the LED such that light emitted by the LED may pass through the window. The window may be made from a material that is at least partially transparent to one or more wavelengths of light emitted by the LED.

An outer surface of the first sidewall may include a male connector, and an outer surface of the second sidewall may include a female connector. The male and/or female connectors may be adapted to couple the first body to a second body having at least one connector that is complementary to the male or female connector.

In some embodiments, the first groove, the second groove, and the cover extend along an entire length of the body. In some embodiments, the LED may be disposed on an inner surface of the bottom wall, and the bottom wall may include a heat vent disposed opposite the inner surface. In some embodiments, the heat vent may include a first recess disposed along an outer surface of the bottom wall. The recess may reduce the material thickness of the body through which heat generated by the LED must travel before being dissipated externally of the body. The recess may also increase the surface area of the body through which heat may dissipate. In some embodiments, the recess may extend along the entire length of the body.

In some embodiments, a second LED may be disposed within the channel, and a second window disposed in the cover adjacent the second LED. In some embodiments, the system may include an end cap disposed at an end of the elongate member. The end cap, the cover, and the body may collectively sealingly enclose an end of the channel. In some embodiments, the LED may be affixed to the bottom wall of the body via a screw extending through a screw hole. The screw hole may terminate at a second recess extending inwardly from the outer surface of the bottom wall.

In some embodiments, the system may further include an elongate second body. The second body may have a first side wall, a second side wall opposite the first side wall, and a bottom wall. The second body may define a lengthwise channel between the first side wall and the second side wall of the second body. The second body may include a first groove disposed along an inner surface of the first side wall, a second groove disposed along an inner surface of the second side wall, and a second cover coupled to the second body via grooves respectively disposed along inner surfaces of the first and second side walls. An outer surface of the first sidewall of the second body may include a male connector, and an outer surface of the second sidewall of the second body may include a female connector. In some embodiments, the female connector of the first body is connected to the male connector of the second body.

In some embodiments, the second body may be inverted relative to the first body, such that the bottom surface of the first body and the bottom surface of the second body face opposed directions. In some embodiments, at least one of the side walls of the first body may define a top surface of the first body, and the first and second bodies may be connected in a linear arrangement such that at least a portion of the top surface of the first body is substantially coplanar with at least a portion of the bottom surface of the second body.

In some embodiments, the first body may be disposed at an angle relative to the second body, such that a first plane in which the inner surface of the bottom wall of the first body lies intersects at an angle with a second plane in which the inner surface of the bottom wall of the second body lies. In some embodiments, the angle may be substantially equal to 60°, 90°, 108°, or 120°.

In some embodiments, a plurality of bodies, including the first body and the second body, may be connected to one-another, and the plurality of bodies may collectively define a closed polygonal arrangement. The polygonal arrangement defined by the plurality of bodies may be a triangle, a square, a rectangle, a pentagon, a hexagon, or other regular or irregular polygon. In some embodiments, each of the bodies of the plurality of bodies may have a heat vent disposed along a respective bottom surface thereof, and the plurality of bodies may collectively define an interior chamber. In some embodiments, each heat vent may be exposed to and configured to dissipate heat into the interior chamber.

In some embodiments, an annular end cap may be provided. In some embodiments, the annular end cap may be connected to each of the plurality of bodies to sealingly enclose an end of a channel defined in each of the respective bodies. In some embodiments, the annular end cap may include a central opening to the interior chamber such that heat may flow out of the interior chamber through the opening in the annular end cap.

In some embodiments, at least one of the side walls of the first body may define a top surface of the first body, and at least one of the side walls of the second body may define a top surface of the second body. The male connector of the first body may be disposed at a midpoint between the bottom surface and the top surface of the first body, and the female connector of the second body may be disposed at a midpoint between the bottom surface and the top surface of the second body. The first and second body may be arranged in either of (i) a linear arrangement in which the second body is inverted relative to the first body and at least a portion of the top surface of the first body is substantially coplanar with at least a portion of the bottom surface of the second body, and (ii) an angled arrangement in which the first body is disposed at an angle relative to the second body, such that a first plane in which the inner surface of the bottom wall of the first body lies intersects at an angle with a second plane in which the inner surface of the bottom wall of the second body lies, a portion of the bottom surface of the first body adjoining a portion of the bottom surface of the second body.

In some embodiments, the one or more LEDs may be UV LEDs. In some embodiments, the system may power the one or more LEDs to emit UV light and deactivate microorganisms in an environment. The system may be configured to dissipate a substantial amount of the heat generated by the one or more LEDs. The system may be configured to provide a seal preventing exposure of the one or more LEDs to a surrounding environment.

Any of the systems disclosed herein may be used in a method for purifying an environment. In some embodiments, a method may include the steps of connecting the female connector of the first body to the male connector of the second body, and emitting light using the one or more LEDs. In some embodiments, the emitted light may be UV light, and the UV light may be used to deactivate microorganisms in an environment.

In some embodiments, a system for applying light to an environment may be provided. The system may include a processor and plurality of LED arrays. In some embodiments, each LED array may include one or more LEDS which may be powered on and off together. In some embodiments, the system may be configured to a apply a pulsed power input to the first LED array during a first timeslot, apply the pulsed power input to a second LED array during a second timeslot, and, if the plurality of LED arrays includes more than two LED arrays, apply the pulsed power input to each remaining LED array in respective timeslots. In some embodiments, these steps may be performed such that power is applied to only one LED array of the plurality of LED arrays at any given time.

In some embodiments, a method for applying light to an environment may be provided. The method may be performed by system including a processor and plurality of LED arrays. In some embodiments, each LED array may include one or more LEDs that are configured to be powered on and off together. The method may include: (a) during a first timeslot, applying a pulsed power input to the a LED array; (b) during a second timeslot, applying the pulsed power input to a second LED array; and (c) if the plurality of LED arrays comprises more than two LED arrays, applying the pulsed power input to each remaining LED array in a respective timeslot. In some embodiments, steps (a)-(c) may be performed such that power is applied to only one LED array of the plurality of LED arrays at any given time.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 4A-4C depict an exemplary combined housing with a shared end cap.

DETAILED DESCRIPTION

Figure 1B:
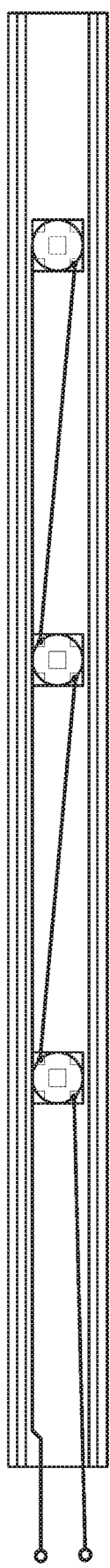
FIGS. 1A-1C depicts an exemplary housing for LEDs.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, expressly recited in the claims, or otherwise dictated by the context of the description, such terms, including, without limitation, top, bottom, side, beside, above, below, under, on top of, upper, lower, left of, right of, in front of, behind, next to, adjacent, opposite, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

As used herein, the terms "optional" and "optionally" mean that the subsequently described, component, structure, element, event, circumstance, property, etc. may or may not be included or occur and that the description includes instances where the component, structure, element, event, circumstance, property, etc. is included or occurs and instances in which it is not or does not.

Figure 1A:
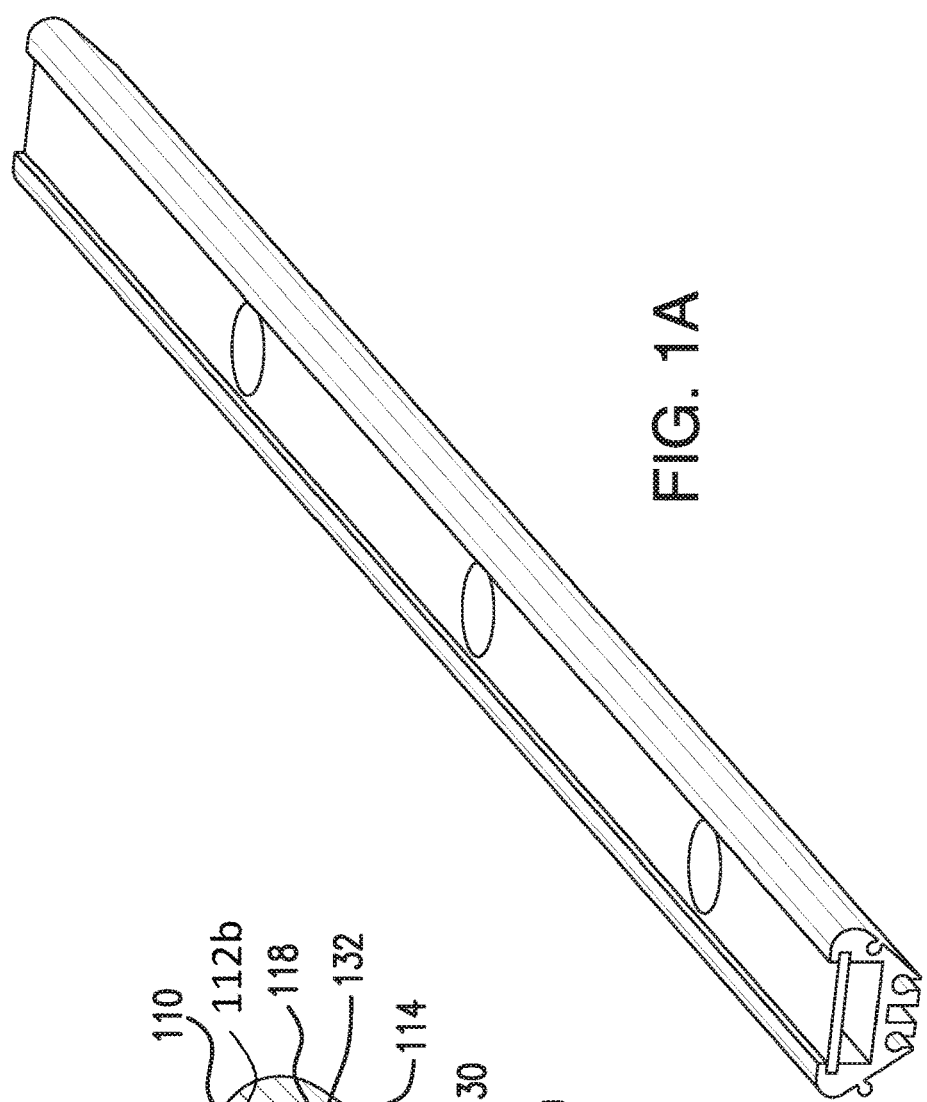
Figure 1C:
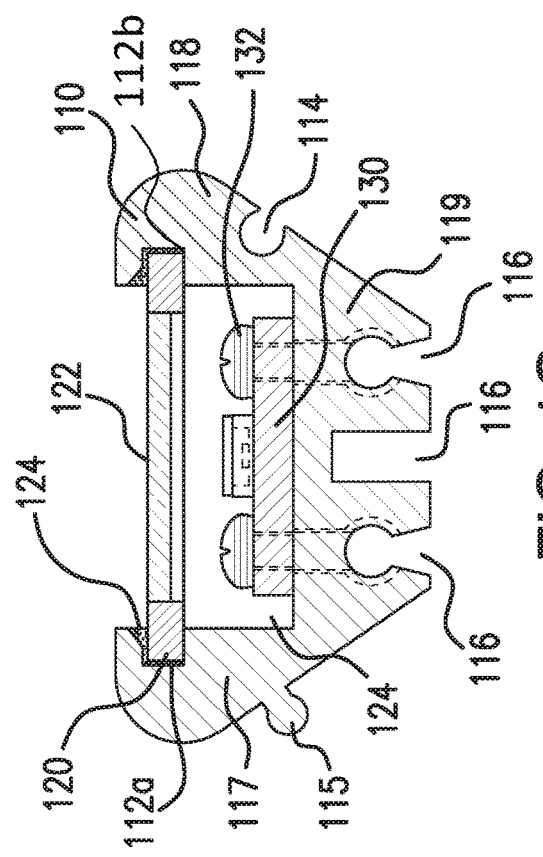

FIGS. 1A-1C illustrate an exemplary housing for an LED. The housing includes a body 110 and a cover 120. The body 110 may be made of a metal or plastic, for example, by extrusion. In some embodiments, the body 110 may be made in part or in whole of aluminum. The cover 120 may be, for example, a plate made from metal or plastic, and in some embodiments, may likewise be made of aluminum. The body may include a first side wall 117, a second side wall 118, and a bottom wall 119. A channel 124 may be disposed between an inner surface of the first side wall 117 and an inner surface of the second side wall 118. As noted above, relative positional terms are used for convenience in describing these arrangements, and are not intended to be limiting. For example, although the bottom wall 119 is shown at the lower end of the body cross-section in FIG. 1C, the body could be inverted in practice.

In some embodiments, grooves 112a, 112b may be disposed along the inner surfaces of the respective side walls 117, 118. The grooves 112a, 112b may extend along a portion or an entire length of the body 110. The cover 120 may be coupled to the body via the grooves 112a, 112b. For example, the cover 120 may be slid into the grooves 112a, 112b such that portions of the cover 120 are at least partially disposed within the grooves 112a, 112b. Optionally, an adhesive 124 may be placed between the cover and the respective grooves to provide an air-tight and/or fluid-tight seal. In some embodiments, the lip of one or more of the grooves may be beveled to facilitate this seal. By providing a fluid-tight seal, the range of applications may be greatly expanded. For example, the system may be used in wet environments or even submerged in water or other liquids to purify or deactivate microorganisms in a range of environments.

In some embodiments, the body may include one or more connectors. For example, a male connector 115 may be provided on an outer surface of the first side wall. A female connector 114 may be provided on an outer surface of the second side wall 118. In some embodiments, the connectors may allow the body of the housing to connect to housings having complementary male or female connectors. Exemplary configurations for connecting one or more housing bodies together are described in greater detail with respect to FIGS. 2A-2D below.

In some embodiments, one or more LEDs may be disposed within the channel 124. With reference to FIG. 1C, an LED 130 may be adapted to emit any desired frequency of visible or nonvisible light. In some embodiments, the LED 130 may be adapted to emit ultraviolet (UV) light. In some embodiments, the LED may be adapted to emit light having a wavelength in a range of 10-400 nm, 100-400 nm, 200-400 nm, 200-300 nm, 300-400 nm, or approximately 365 nm. In some embodiments, the LED 130 may be affixed to the body 110 within the channel 124. For example, the LED 130 may be mounted to a board, and the board may be affixed to the body via mounting screws 132. In some embodiments, the LED 130 may be affixed to a top surface of the bottom wall 119 of the body 110. In some embodiments, the LED 130 may be affixed to the bottom wall 119 of the body 110 via a screw 132 extending through a screw hole, and the screw hole may terminate at a recess 116 extending inwardly from the outer surface of the bottom wall. In this arrangement, heat generated by the LED may flow through the screw body and may dissipate via the recess.

In some embodiments, a heat vent may be disposed along a lower surface of the bottom wall 119. In some embodiments, the heat vent may include one or more recesses which may reduce the material thickness of the body through which heat generated by the LED must travel before being dissipated externally of the body. In some embodiments, the recess or recesses may also increase the surface area of the body through which heat may dissipate. In some embodiments, the heat vent may include one, two, or three recesses. The recess(es) may extend along a portion or an entire length of the body. In some embodiments, screws used to mount the LED may terminate at one or more of the recesses. For example, in the embodiment shown in FIG. 1C, mounting screws terminate at two of the recesses 116 to facilitate heat flow into and from the recesses 116.

In some embodiments, one or more windows 122 may be disposed in the cover 120. The window 122 may be at least partially transparent to one or more wavelengths of light emitted by the LED 130, and the window 122 may be disposed adjacent the LED 130 such that light generated by the LED may pass through the window 122 and reach an area external to the channel 124. In some embodiments, the window 122 may be made of quartz glass. In some embodiments, a series of LEDs may be spaced along the length of the body, and a corresponding window may be disposed above each. Examples of such arrangements are generally depicted in FIGS. 1A and 1B. In some embodiments, the series of LEDs may be powered by a shared circuit 134. In this manner, the LEDs may be controlled together.

Figure 2B:
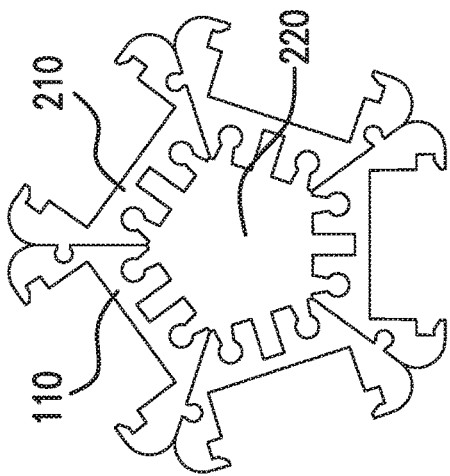
FIGS. 2A-2D depict exemplary arrangements for combining LED housings.
Figure 2C:
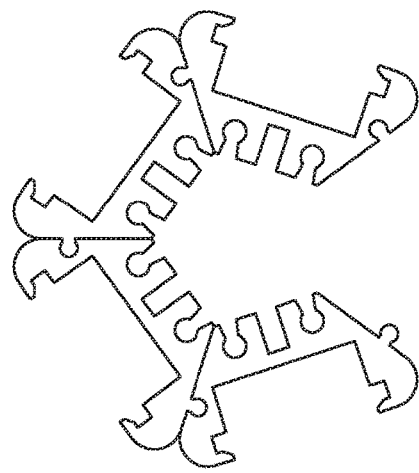
Figure 2D:
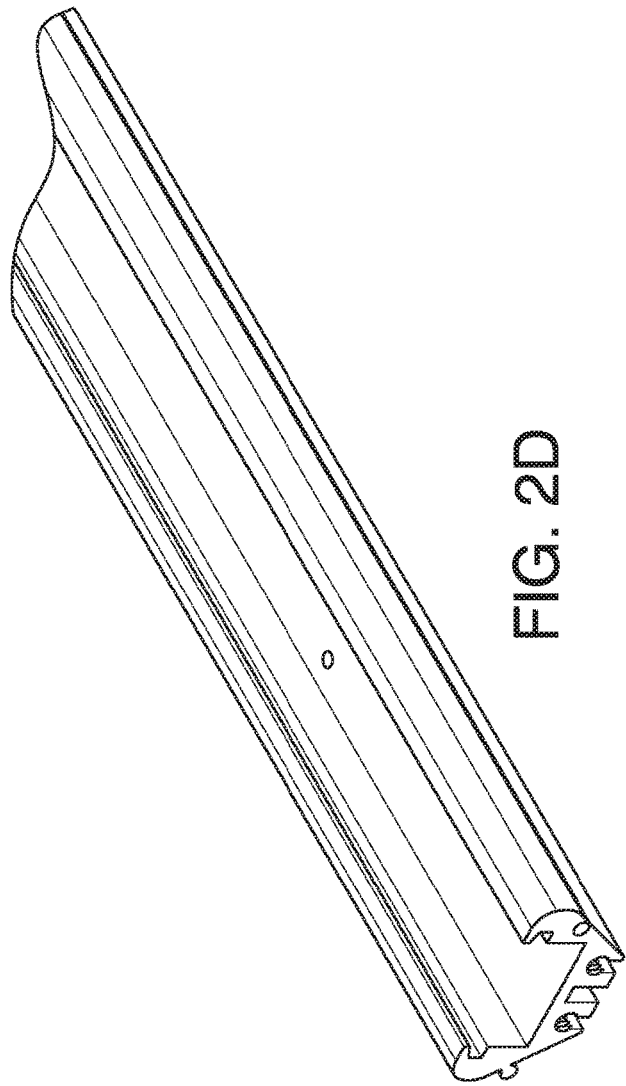
Figure 2A:
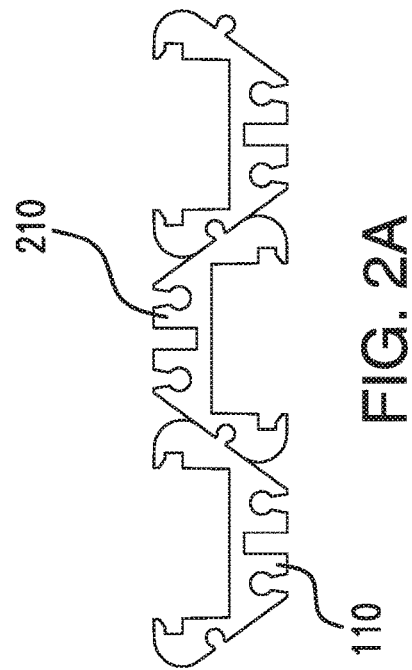

FIGS. 2A-2C depict exemplary arrangements of two or more housing bodies. For example, a first body 110 as described with respect to FIGS. 1A-1C may be coupled to a second body 210. Optionally, the second body may be structurally similar or identical to the first body. For example, the second body 210 may have a channel defined between opposed side walls, a bottom wall, and a cover, and one or more LEDs may be disposed within the channel, as generally described above. In other embodiments, the second body 210 may simply have one or more connectors that are complementary to the connectors of the first body 110.

FIG. 2A shows an exemplary linear arrangement of housing bodies. In the illustrated arrangement, the second body is inverted relative to the first body such that the bottom surfaces of the first and second bodies face opposed directions. A top surface, or portion thereof, of the first body 110 may be substantially coplanar with the bottom surface, or portion thereof, of the second body 210. Conversely, a bottom surface, or portion thereof, of the first body 110 may be substantially coplanar with the top surface, or portion thereof, of the second body 210. Additional bodies, beyond the first and second bodies, may be added to this linear arrangement as desired. FIG. 2A, for example, shows three such bodies connected in a linear arrangement, but similar arrangements could be made using two, three, four, five, six, or more bodies. Optionally, each of those bodies may have the same modular structure described above. In this embodiment the final structure effectively becomes either a single- or double-sided UV light emitting panel, ideal for treating large planar surfaces, such as food conveyor belts.

FIG. 2B depicts an angled arrangement in which the first body 110 is disposed at an angle relative to the second body 210. In the illustrated embodiment, a plane in which the inner surface of the bottom wall of the first body lies intersects at an angle with a second plane in which the inner surface of the bottom wall of the second body lies. In some embodiments, the angle defined between these two planes may be substantially equal to 60°, 90°, 108°, or 120°. As shown in FIG. 2B, a portion of the bottom surface of the first body may adjoin a portion of the bottom surface of the second body. It is often preferred that the angle of 110 corresponds to the chosen LED diode emission angle and is chosen so the adjacent LED module in the array's emission energy overlaps with its own emission energy, in such a way as creating a uniform field of UV energy for effective total treatment (for either annular or planar assemblies).

Additional bodies, beyond the first and second bodies, may be angularly connected to one another such that a plurality of bodies may collectively define a closed polygonal arrangement. In some embodiments, each of the bodies may have the same modular structure described above. In some embodiments, the closed polygonal arrangement may be triangular, square, rectangular, pentagonal, hexagonal, or it may have another polygonal shape. In some embodiments, the bodies may collectively define an interior chamber within the polygonal arrangement. Each of the bodies of the polygonal arrangement may have a heat vent disposed along a respective bottom surface thereof, such that each heat vent is exposed to and configured to dissipate heat into the interior chamber. In some embodiments, a fan or pump may be disposed within or adjacent to the interior chamber such that the fan or pump may cause air or liquid to flow through the interior chamber and dissipate heat externally of the system. This may be advantageous in cases where high power LED's are used.

In some embodiments, the first body 110 may be arranged to be disposed in either the linear arrangement shown in FIG. 2A or the angular arrangements shown in FIG. 2B or 2C. FIG. 2D shows a single body, which may be used in the arrangements shown in FIGS. 2A-C. In some embodiments, the male and female connectors may be disposed at a midpoint between the bottom surface and the top surface of the respective bodies, thereby allowing a body to be inverted and aligned next to an adjacent body without substantially changing the vertical position of the connector on the inverted body. In some embodiments, the first body 110 may be connected to other bodies in either arrangement by an operator in the field or during manufacture of a combined assembly.

Figure 3A:
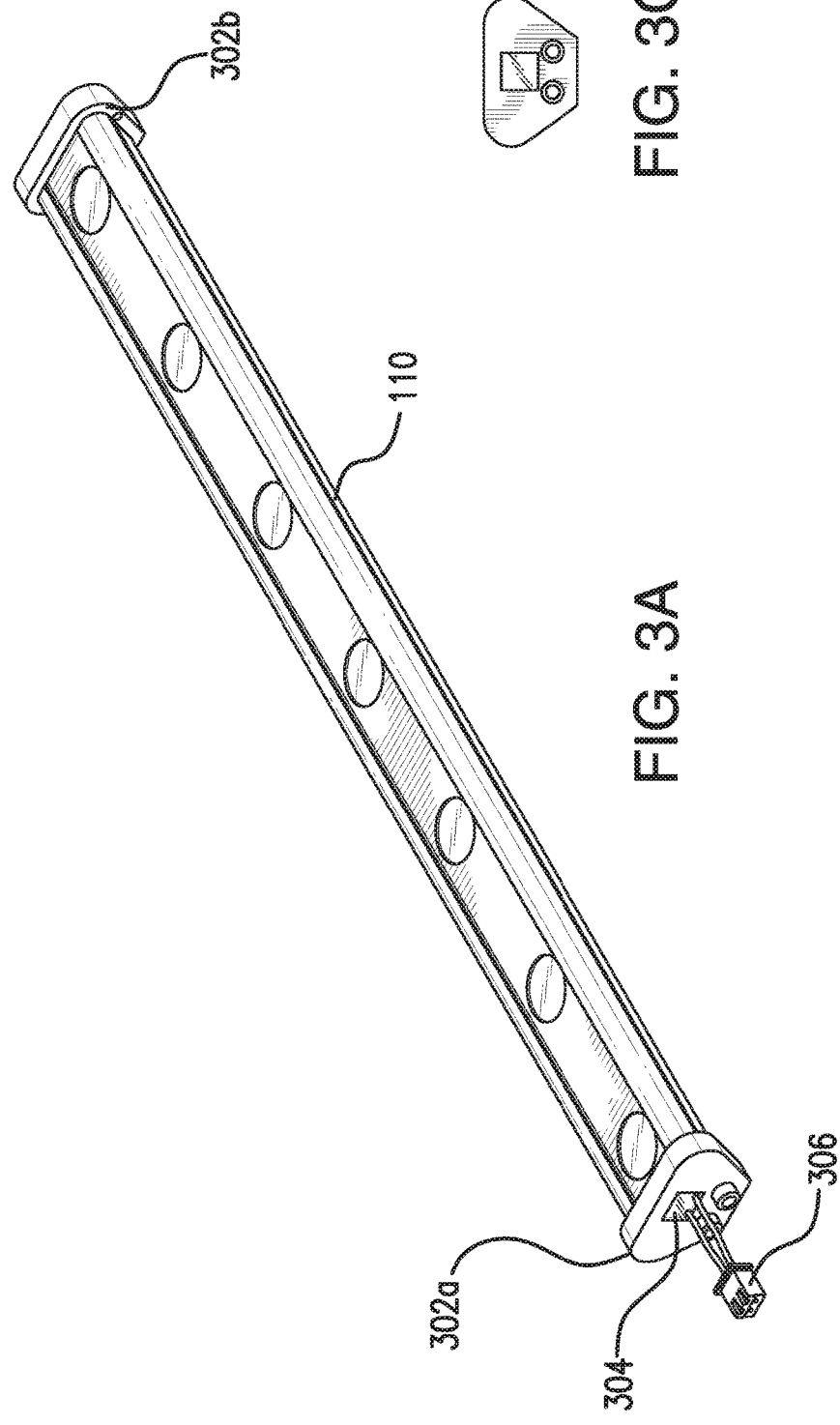
FIGS. 3A-3C depict an exemplary LED housing with an end cap.
Figure 3C:
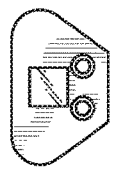
Figure 3B:
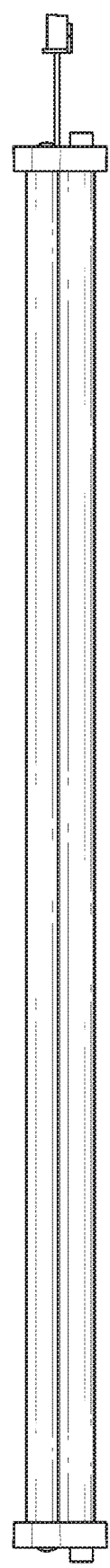

FIGS. 3A-3C and 4A-4C show exemplary end cap arrangements. FIG. 3A shows a body 110 having end caps 302*a*, 302*b* on its opposed ends. The end caps 302 may sealingly enclose the channel defined within the body. For example, a silicone gasket may be provided between the cap 302 and the body 110 to form an air-tight and/or liquid-tight seal. Electrical power may be provided to the LEDs via wires extending through a sealed port 304, which may be a silicone seal in some embodiments, in the end cap 302*a*. The wires may extend to an electrical plug 306. In other embodiments, metal lugs may be provided in place of the plug. These metal lugs may be arranged to slide into a neighboring module, such that electrical power may be shared between the two modules. In some embodiments, the metal lugs or a conductor attached thereto may extend through the material used to create the end cap itself, thereby obviating the need for a sealed port. FIGS. 3B and 3C show alternate perspectives of the body of FIG. 3A.

FIG. 4A shows a system 400 of five modular bodies connected in a pentagonal arrangement similar to that shown in FIG. 2B. The system 400 includes an annular end cap 402, which may be connected to each of the plurality of modular bodies to sealingly enclosing an end of a channel defined in each of the respective bodies. The annular end cap 402 may also include a central opening to an interior chamber formed by the modular bodies such that heat may flow out of the interior chamber through the opening in the annular end cap 402. The term annular is used to indicate that the shape has an opening in its inner area and is not limited to any particular shape. The end cap shown in FIG. 4A is substantially pentagonal, but it may take other shapes to reflect the shape of and/or number of modules used in a given arrangement.

As described above with respect to the embodiment of FIG. 3A, a silicone gasket may be provided between the cap 402 and the respective bodies to form an air-tight and/or liquid-tight seal. Electrical power may be provided to the LEDs in the modular bodies via wires extending through sealed ports 404, which may be a silicone seal in some embodiments, in the end cap 402. The wires may extend to an electrical plug 406. In other embodiments, metal lugs may be provided in place of the plug. These metal lugs may be arranged to slide into a neighboring system, such that electrical power may be shared between the two systems. In some embodiments, the metal lugs or a conductor attached thereto may extend through the material used to create the end cap itself, thereby obviating the need for a sealed port. FIGS. 4B and 4C show alternate perspectives of the system of FIG. 4A.

Figure 5:
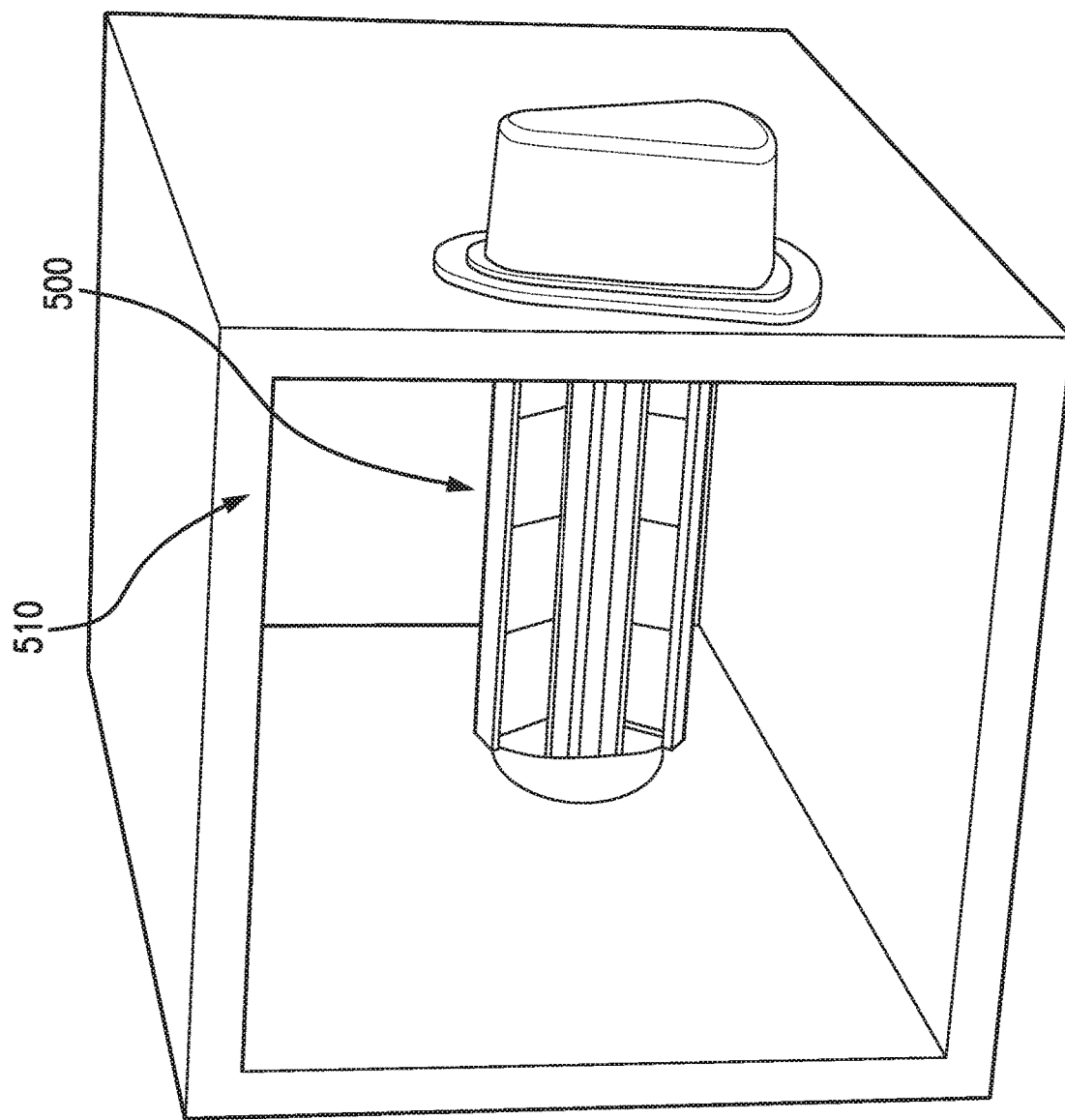
FIG. 5 shows an exemplary LED system arranged for use within an HVAC system.

FIG. 5 shows an exemplary LED system 500 arranged for use within a duct 510 of an HVAC system. The LED system 500 of FIG. 5 may include any of the systems or components described above with respect to FIGS. 1-4. The system 500 is shown within an HVAC duct merely by way of as example. For example, the system 500 may be used in a wide range of environments where a purification function is desired, including in air purification or filtration systems, water treatment or filtration systems, food preparation or treatment systems, or other residential or industrial applications.

Figure 6:
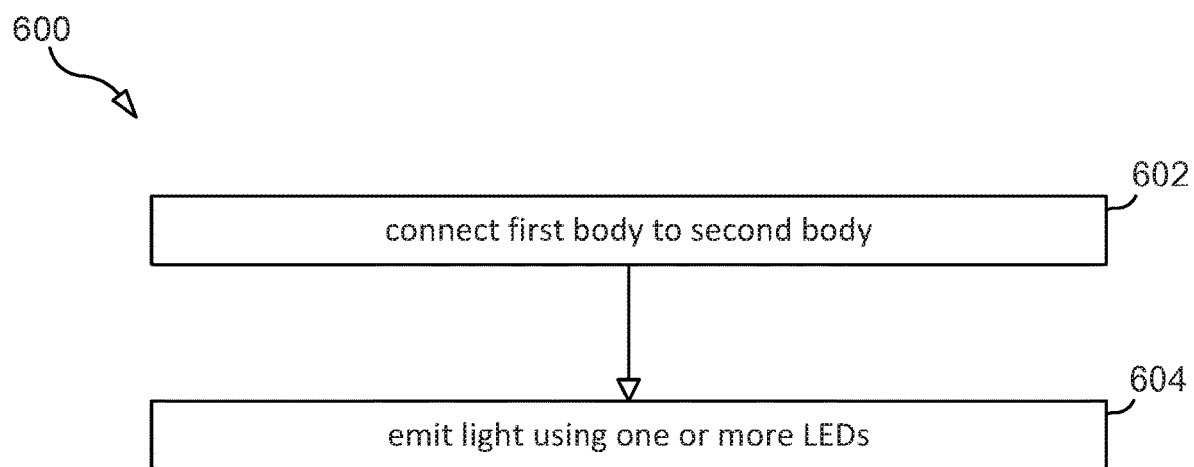
FIG. 6 shows an exemplary method for using an LED system.

FIG. 6 shows an exemplary method 600 for using an LED system. The LED system 500 of FIG. 5 may include any of the systems or components described above with respect to FIGS. 1-4. In step 602, a first body may be connected to a second body. For example, a female connector of the first body 110 may be connected to a male connector of a second body in any of the arrangements described above, and in particular, with reference to FIGS. 2A-2C. In step 604, light may be emitted using one or more LEDs disposed within the first and/or second body. For example, power may be applied to the LEDs via the plugs or metal lugs and circuitry generally described above with respect to FIGS. 1B, 3A, 3B, 4A, and 4B. This may cause light to be emitted from the LEDs and through one or more windows disposed adjacent to those LEDs. The emitted light may be UV light, and it may be used to purify or deactivate microorganisms in an environment.

Figure 7:
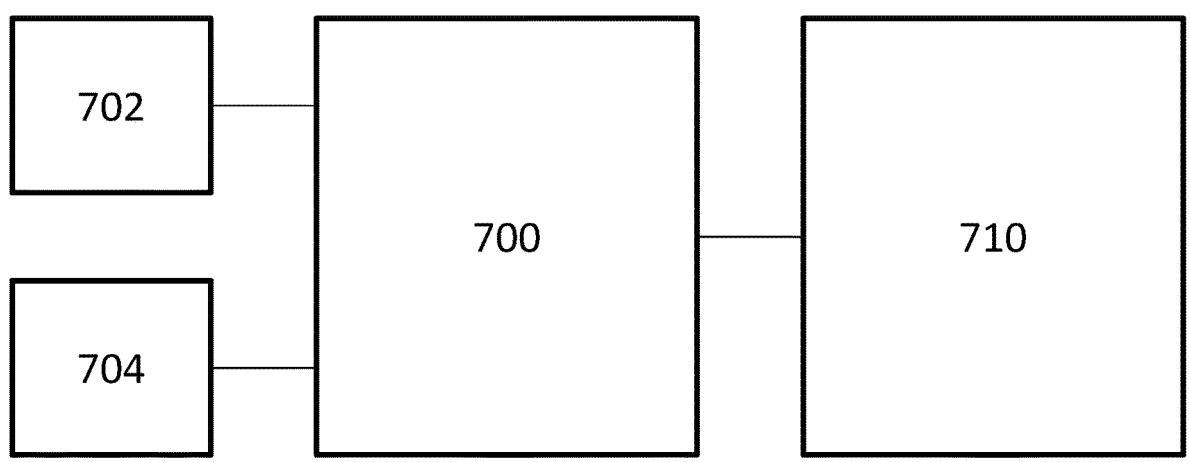
FIG. 7 shows an exemplary system for controlling activation of LED arrays.

FIG. 7 shows an exemplary system for controlling activation of LED arrays. The system may include a processor 700 and one or more LED arrays 710, which may be controlled by the processor 700. The system may be used to control arrays of LEDs within the modular bodies, as described with respect to FIGS. 1-6. This system may be used to control any of the arrangements described above, including LED arrays of a single body, two, three, four, or five (etc.) bodies connected together. In some embodiments, the control system may be used to control the LED arrays of the pentagonal arrangement shown in FIGS. 4A-4C. The system may include a power source 702. In some embodiments, the power source 702 may be a power cable which may be plugged into an electrical outlet, or it may be a portable power source such as a battery. In some embodiments, the system may include an indicator 704, which may include one or more status indicators (e.g., colored LEDs). The status indicators may indicate status information, such as whether the system is receiving power, whether the system is in operational condition, or whether the system is actively supplying power to one or more LED arrays.

In some embodiments, the processor 700 may control which of the one or more LED arrays 710 are receiving a power input at any given time. For example, an individual power input may be supplied to each LED strip in the total LED array sequentially. In some embodiments, the power input may be pulsed at a frequency. The LEDs receiving a pulsed power input may cycle on and off at the frequency of the pulsed power. In some embodiments, the pulse frequency may range from 50 to 200 Hz, though the selected frequency can be higher or lower depending on the conditions required to create the performance desired. In some embodiments, the pulse frequency may range from 1 Hz to 10,000 Hz. In some embodiments, the pulse frequency may be selected to maximize the lethality of resulting UV radiation to one or more microbial species.

In some embodiments, each LED array 710 may receive an input power for a given interval. After the programmed time "on" interval is reached for a given single array, the input current may then be diverted and fed into the next LED array in the sequence. Once the next LED array has completed its power on interval, power may then be transferred to the next LED array. This process may be repeated until each of the LED arrays has been powered on during a respective interval. In some embodiments, the sequence may be controlled such that only one LED array receives power at any given time. In some embodiments, the power input pulse may have the same magnitude and frequency when applied to each of the LED arrays in the sequence. In some embodiments, after all the LED arrays in the sequence have been energized and timed out, the process may immediately reset, starting again on the first LED array in the sequence, proceeding to the second, and so on.

In some embodiments, the collection of one or more LED arrays 710 may have active and inactive cycles. During active cycles, power may be rotated through the individual LED arrays as described above. During inactive cycles, power may not be applied to any of the one or more LED arrays 710, such that all of the LED arrays are powered down. Interposing inactive cycles between active cycles may allow the system as a whole to cool down, allowing the system to operate in higher-temperature environments, and expanding the working life of the system.

The lengths of the active and inactive cycles may be varied. For example, in a five-array pentagonal arrangement, a first array may be powered for a predetermined time (e.g., 2 seconds), then a second array may be powered for the same amount of time, and so on until all five arrays have been powered during a respective timeslot. In some embodiments, this single iteration through each array in the system may be considered a first active cycle (e.g., 10 seconds). In other embodiments, an active cycle may include multiple iterations powering each LED array in the sequence (e.g., an active cycle of six iterations through the five-array system, with each array being powered for 2-second intervals would be a 60-second active cycle). The system may then enter an inactive cycle, allowing the system to cool, before returning to another active cycle. The length of the inactive cycles may be selected to control the percentage of the time that the system is active. For example, in embodiments where active and inactive cycles are the same length, the system may be powered on and creating heat 50% of the time. If more time for heat dissipation is needed, or if energy savings is desired, the length of the inactive cycles may be increased.

Figure 8:
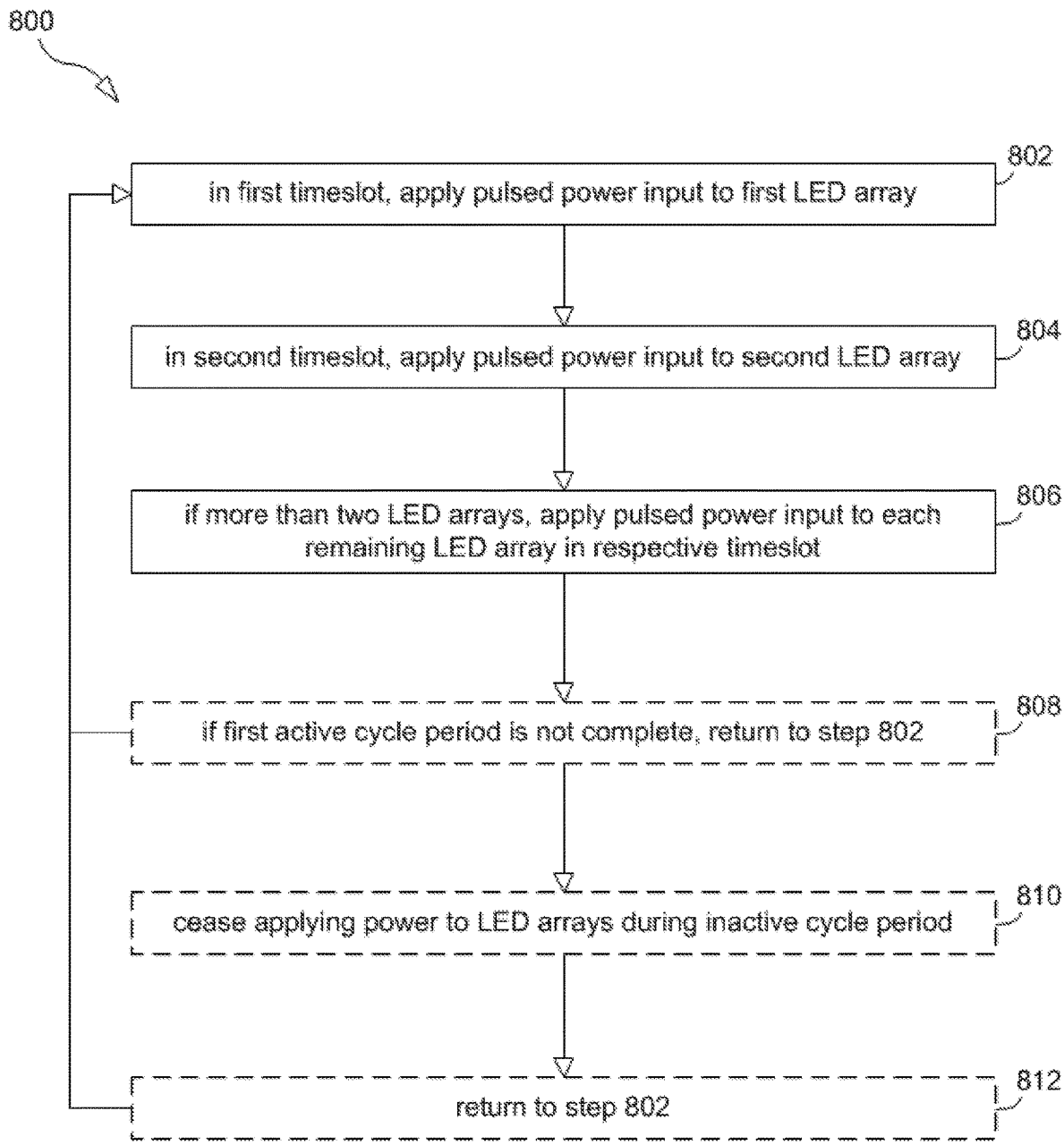
FIG. 8 shows an exemplary method 800 for controlling activation of LED arrays.

FIG. 8 shows an exemplary method 800 for using the system of FIG. 7. In some embodiments, the method 800 may be performed by a system including a processor and a plurality of LED arrays, each of which may include one or more LEDs that are configured to be powered on and off together. The plurality of LED arrays may include at least a first LED array and a second LED array. In step 802, during a first timeslot, a pulsed power input may be applied to the first LED array. In step 804, during a second timeslot, the pulsed power input may be applied to the second LED array. In step 806, if the plurality of LED arrays includes more than two LED arrays, the pulsed power input may be applied to each of the remaining LED arrays in respective timeslots. For example, power may be applied to a third LED array in a third timeslot, power may be applied to a fourth LED array in a fourth timeslot, and so on. In some embodiments, steps 802-806 may be performed such that power is applied to only one LED array of the plurality of LED arrays at any given time.

Steps 808-812 reflect optional steps which may be used in conjunction with alternating active and inactive cycles. In step 808, steps 802-806 may be repeated one or more times during a first active cycle period. In step 810, after the first active cycle period is complete, the system may cease applying power to the plurality of LED arrays during an inactive cycle period. In step 812, after the inactive cycle period is complete, the system may again return to perform steps 802-806 one or more times during a second active cycle period. Additional active and inactive cycles may be repeated indefinitely, or until the system is powered down or times out pursuant to a user or programmed instruction.

The above-described control system and method offers several distinct advantages. By pulsing the individual LED arrays, it is possible to turn on and off the LEDs as desired. The longer the LED is off, the less heat is generated and the lower the junction temperature of the LED will be. This lower temperature significantly increases the working life of the LEDs in the system. Further, by pulsing each LED on and then off, it is possible to drive each of the LED's at a higher current, providing more delivered germicidal UV output energy, while keeping a lower junction temperature as compared to an equivalently current driven non-pulsed LED. This allows the germicidal efficacy of the system to be improved at the same time as the LED life is increased. Relative to an LED that is not pulsed with equivalent average power consumption, a pulsed LED may have higher peak power output. Pulsed LEDs are found to provide improved germicidal and anti-microbial activity relative to LEDs that are not pulsed.

Moreover, because heat dissipation is improved, it is possible to use smaller heatsinks for a given array, thereby reducing manufacturing costs. Additionally, for a given heatsink arrangement, the LED arrays can be used in hotter operating environments than would otherwise be possible.

In some embodiments, total power consumption can also be reduced. By pulsing each LED array in the system at a different time, the total current for the full system may be proportionally reduced by the number of actual individual LED arrays in the system. Considering a system with 10 LED arrays, for example, in which each array draws 1 amp of current, the current required for a full non-pulsed array would be 10 amps. By utilizing the method described above in which power is supplied to each LED array in sequence, the power requirement for the full system drops to just 1 amp. This allows circuit elements (e.g., integrated circuit components, traces, wire gauges, connectors, etc.) that are shared between the LED arrays to be sized for just one amp, as opposed to 10 amps. In the above example, a wire trace may be sized such that it can safely carry 1 amp, but would fail under a current of 10 amps. This may significantly reduce both component costing and the overall packaging size of all the components needed (making the final product less expensive and smaller). In some embodiments, this may also require less input current from the facility in which the system is installed, since only one of the LED arrays may draw current at any given time.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the recited subject matter requires features or combinations of features other than those expressly recited in the numbered embodiments. Accordingly, the scope of this disclosure is intended to include all modifications and variations encompassed within the spirit and scope of the following appended embodiments. Any positional terms used in these numbered embodiments are intended in a relative—not absolute— sense, such that the claimed devices, components, and systems may be rotated or their orientation changed without effect vis-à-vis the scope of the following numbered embodiments.

The invention claimed is:

1. A system for applying light to an environment, the system comprising:
    an elongate first body comprising a first side wall, a second side wall opposite the first side wall, and a bottom wall, the first body defining a lengthwise channel between the first side wall and the second side wall;
    a first groove disposed along an inner surface of the first side wall;
    a second groove disposed along an inner surface of the second side wall;
    a cover, the cover being coupled to the first body via the first groove and the second groove, wherein the first body and the cover collectively enclose at least a portion of the channel;
    a light emitting diode (LED) disposed within the channel;
    a window comprising a material that is at least partially transparent to one or more wavelengths of light emitted by the LED, the window being disposed in the cover adjacent the LED such that light emitted by the LED may pass through the window;
    wherein an outer surface of the first sidewall comprises a male connector, and an outer surface of the second sidewall comprises a female connector, the male and/or female connectors being adapted to couple the first body to a second body having at least one connector that is complementary to the male or female connector.

2. The system of claim 1, wherein the first groove, the second groove, and the cover extend along an entire length of the body.

3. The system of claim 1, wherein the LED is disposed on an inner surface of the bottom wall, and the bottom wall comprises a heat vent disposed opposite the inner surface.

4. The system of claim 3, wherein the heat vent comprises a first recess disposed along an outer surface of the bottom wall, the recess decreasing the material thickness of the body through which heat generated by the LED must travel before being dissipated externally of the body, the recess also increasing the surface area of the body through which heat may dissipate.

5. The system of claim 4, wherein the recess extends along the entire length of the body.

6. The system of claim 1, further comprising:
    a second LED disposed within the channel; and
    a second window disposed in the cover adjacent the second LED.

7. The system of claim 1, further comprising an end cap disposed at an end of the elongate member, the end cap, the cover, and the body collectively sealingly enclosing an end of the channel.

8. The system of claim 1, wherein the LED is affixed to the bottom wall of the body via a screw extending through a screw hole, the screw hole terminating at a second recess extending inwardly from the outer surface of the bottom wall.

9. The system of claim 1, further comprising:
    an elongate second body comprising a first side wall, a second side wall opposite the first side wall, and a bottom wall, the second body defining a lengthwise channel between the first side wall and the second side wall of the second body;

a first groove disposed along an inner surface of the first side wall;

a second groove disposed along an inner surface of the second side wall;

a second cover coupled to the second body via grooves respectively disposed along inner surfaces of the first and second side walls;

wherein an outer surface of the first sidewall of the second body comprises a male connector, and an outer surface of the second sidewall of the second body comprises a female connector; and the female connector of the first body is connected to the male connector of the second body.

10. The system of claim 9, wherein the second body is inverted relative to the first body, such that the bottom surface of the first body and the bottom surface of the second body face opposed directions.

11. The system of claim 10, at least one of the side walls of the first body defines a top surface of the first body, and the first and second bodies are connected in a linear arrangement such that at least a portion of the top surface of the first body is substantially coplanar with at least a portion of the bottom surface of the second body.

12. The system of claim 9, wherein the first body is disposed at an angle relative to the second body, such that a first plane in which the inner surface of the bottom wall of the first body lies intersects at an angle with a second plane in which the inner surface of the bottom wall of the second body lies.

13. The system of claim 12, wherein the angle is substantially equal to 60°, 90°, 108°, or 120°.

14. The system of claim 11, wherein the first body and the second body are comprised within a plurality of bodies connected to one-another, the plurality of bodies collectively defining a closed polygonal arrangement.

15. The system of claim 14, wherein the polygonal arrangement defined by the plurality of bodies is selected from a group consisting of: a triangle, a square, a rectangle, a pentagon, and a hexagon.

16. The system of claim 14, wherein each of the bodies of the plurality of bodies has a heat vent disposed along a respective bottom surface thereof, the plurality of bodies collectively defining an interior chamber, each heat vent being exposed to and configured to dissipate heat into the interior chamber.

17. The system of claim 16, further comprising an annular end cap, the annular end cap being connected to each of the plurality of bodies to sealingly enclose an end of a channel defined in each of the respective bodies, the annular end cap comprising a central opening to the interior chamber such that heat may flow out of the interior chamber through the opening in the annular end cap.

18. The system of claim 9, further wherein:

at least one of the side walls of the first body defines a top surface of the first body, and at least one of the side walls of the second body defines a top surface of the second body; and the male connector of the first body is disposed at a midpoint between the bottom surface and the top surface of the first body, and the female connector of the second body is disposed at a midpoint between the bottom surface and the top surface of the second body, such that the first and second body may be arranged in either of the following two configurations:

(i) a linear arrangement in which the second body is inverted relative to the first body and at least a portion of the top surface of the first body is substantially coplanar with at least a portion of the bottom surface of the second body; and (ii) an angled arrangement in which the first body is disposed at an angle relative to the second body, such that a first plane in which the inner surface of the bottom wall of the first body lies intersects at an angle with a second plane in which the inner surface of the bottom wall of the second body lies, a portion of the bottom surface of the first body adjoining a portion of the bottom surface of the second body.

19. The system of claim 1, wherein the one or more LEDs are ultraviolet (UV) LEDs.

20. The system of claim 1, wherein the system is configured to power the one or more LEDs to emit UV light and deactivate microorganisms in an environment.

* * * * *